Figure 1A:
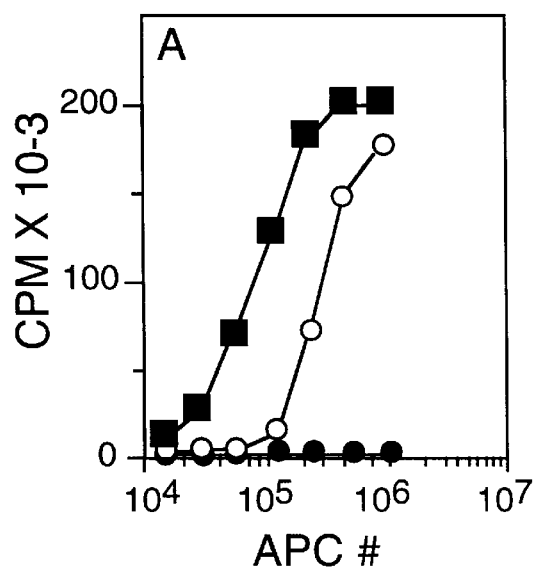

US005951975A

United States Patent [19]
Falo, Jr. et al.

[11] Patent Number: 5,951,975
[45] Date of Patent: *Sep. 14, 1999

[54] INDUCTION OF CTLS SPECIFIC FOR NATURAL ANTIGENS BY CROSS PRIMING IMMUNIZATION

[75] Inventors: Louis D. Falo, Jr., Pittsburgh, Pa.; Kenneth L. Rock, Chestnut Hill, Mass.

[73] Assignees: University of Pittsburgh, Pittsburgh, Pa.; Dana-Farber Cancer Institute, Boston, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/675,332

[22] Filed: Jun. 28, 1996

[51] Int. Cl.$^6$ .......................... A01N 63/00; A61K 39/12; A61K 39/00; A61K 39/29
[52] U.S. Cl. .................. 424/93.2; 424/277.1; 424/227.1; 424/208.1; 424/204.1; 424/93.21; 514/2; 514/21
[58] Field of Search .............................. 424/277.1, 204.1, 424/208.1, 227.1, 93.2, 93.21; 514/2, 21

[56] References Cited

U.S. PATENT DOCUMENTS

| | | | |
|---|---|---|---|
| 5,045,320 | 9/1991 | Mescher | 424/450 |
| 5,399,346 | 3/1995 | Anderson et al. | 424/93.21 |

OTHER PUBLICATIONS

Williams et al., "Introduction of Foreign Genes into Tissues of Living Mice by DNA–Coated Microprojectiles", *Proc. Natl. Acad. Sci. USA*, Apr. 1991, pp. 2726–2730, vol. 88.

Boon, "Toward a Genetic Analysis of Tumor Rejection Antigens", *Advances in Cancer Research*, 1992, pp. 177–211, vol. 58.

Tang et al., "Genetic Immunization is a Simple Method for Eliciting an Immune Response", *Nature*, Mar. 12, 1992, pp. 152–154, vol. 356.

Montgomery et al., "Heterologous and Homologous Protection Against Influenza A by DNA Vaccination: Optimization of DNA Vectors", *DNA and Cell Biology*, 1993, pp. 777–783, vol. 12, No. 9.

Ulmer et al., "Heterologous Protection Against Influenza by Injection of DNA Encoding a Viral Protein", *Science*, Mar. 19, 1993, pp. 1745–1749, vol. 259.

Nabel et al., "Direct Gene Transfer with DNA–Liposome Complexes in Melanoma: Expression, Biologic Activity, and Lack of Toxicity in Humans", *Proc. Natl. Acad. Sci. USA*, Dec. 1993, pp. 11307–11311, Vol. 90.

Fynan et al., "DNA Vaccines: Protective Immunizations by Parenteral, Mucosal, and Gene–Run Inoculations" *Proc. Natl. Acad. Sci. USA*, Dec. 1993, pp. 11478–11482, vol. 90.

Nabel et al., "Immunotherapy for Cancer by Direct Gene Transfer into Tumors", *Human Gene Therapy*, 1994, pp. 57–77, vol. 5.

Flamand et al., "Murine Dendritic Cells Pulsed In Vitro with Tumor Antigen Induce Tumor Resistance In Vivo", *Eur. J. Immunol.*, 1994, pp. 605–610, vol. 24.

Wahl et al., "Generation of Therapeutic T–Lymphocytes After In Vivo Tumor Transfection with an Allogeneic Class I Major Histocompatibility Complex Gene", *Journal of Immunotherapy*, 1995, pp. 1–11, vol. 17.

Nabel et al., "Direct Gene Transfer for Treatment of Human Cancer", *Annals New York Academy of Sciences*, 1995, pp. 227–231, vol. 772.

Sato et al., "Human Immune Response to DNP–Modified Autologous Cells After Treatment with a DNP–Conjugated Melanoma Vaccine", *Clinical Immunology and Immunopathology*, Jan. 1995, pp. 35–43, vol. 74, No. 1.

Kovacsovics–Bankowski et al., "A Phagosome–to–Cytosol Pathway for Exogenous Antigens Presented on MHC Class I Molecules", *Science*, Jan. 13, 1995, pp. 243–246, vol. 267.

Sun et al., "In Vivo Cytokine Gene Transfer by Gene Gun Reduces Tumor Growth in Mice", *Proc. Natl. Acad. Sci. USA*, Mar. 1995, pp. 2889–2893, vol. 92.

Donnelly et al., "Preclinical Efficacy of a Prototype DNA Vaccine: Enhanced Protection Against Antigenic Drift in Influenza Virus", *Nature Medicine*, Jun. 1995, pp. 583–587, vol. 1, No. 6.

Kundig et al., "Fibroblasts as Efficient Antigen–Presenting Cells in Lymphoid Organs", *Science*, Jun. 2, 1995, pp. 1343–1347, vol. 268.

Porgador et al., "Bone Marrow–Generated Dendritic Cells Pulsed with a Class I–Restricted Peptide are Potent Inducers of Cytotoxic T Lymphocytes", *J. Exp. Med.*, Jul. 1995, pp. 255–259, vol. 182.

Mayordomo et al., "Bone Marrow–Derived Dendritic Cells Pulsed with Synthetic Tumour Peptides Elicit Protective and Therapeutic Antitumour Immunity", *Nature Medicine*, Dec. 1995, pp. 1297–1302, vol. 1, No. 12.

Arnold et al J Exp. Medicine vol. 182 pp. 885–889 (Sep. 1995).

Clerici et al, J. Immunology vol. 146, pp. 2214–2219 (Apr. 1991).

*Primary Examiner*—Paula K. Hutzell
*Assistant Examiner*—Geetha P. Bansal
*Attorney, Agent, or Firm*—Diane R. Meyers; Arnold B. Silverman; Eckert Seamans Cherin & Mellott, LLC

[57] ABSTRACT

The present invention relates to prophylactic and therapeutic methods of anti-tumor immunization. These methods are based on cross-priming a mammalian host to natural MHC class I restricted tumor antigens with an artificial tumor antigen. A primary tumor is resected from the patient and a population of tumor cells are cultured in vitro. These cultured tumor cells are loaded with an artificial target antigen. The loaded tumor cells are inactivated and introduced into the patient either simultaneous or subsequent to a direct immunization of the patient with the same or substantially the same artificial target antigen. This method of coupled host immunization promotes a tumor specific cytotoxic T lymphocyte (CTL) immune response against multiple, undefined natural tumor antigens expressed on the unmodified tumor cell surface.

22 Claims, 8 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

```
Ser Ile Ile Asn Phe Glu Lys Leu
1               5
```

INDUCTION OF CTLS SPECIFIC FOR NATURAL ANTIGENS BY CROSS PRIMING IMMUNIZATION

The invention described herein was made in the course of work supported in part by Public Health Service, Grant No. AR01-1884 from the United States National Institutes of Health. The United States Government has certain rights in this invention.

1. INTRODUCTION

The present invention relates to prophylactic and therapeutic methods of anti-tumor immunization. At the core of the invention are anti-tumor immunization methods based on cross-priming a mammalian host to natural MHC class I restricted tumor antigens with an artificial tumor antigen (ATA). This specification discloses treatment of a primary tumor in a mammalian host, preferably a human host. The primary tumor is resected from the human patient and a population of tumor cells are cultured in vitro. These cultured tumor cells are loaded with the artificial target antigen. The loaded tumor cells are inactivated and introduced into the patient either simultaneous or subsequent to a direct immunization of the patient with the artificial target antigen. As a by-product of the immune response to the artificial target antigen on the engineered tumor cell surface, induction of a tumor specific cytotoxic T lymphocyte (CTL) immune response is generated against multiple, undefined natural tumor antigens expressed on the unmodified tumor cell surface.

2. BACKGROUND OF THE INVENTION

Cytotoxic T-lymphocytes (CTLs) are a critical component of effective human immune responses to tumors or viral infections. Cytotoxic T-lymphocytes destroy neoplastic cells or virus infected cells through recognition of antigenic peptides presented by MHC class I molecules on the surface of the affected target cells. These antigenic peptides are degradation products of foreign proteins present in the cytosol of the affected cell, which are processed and presented to CTLs through the endogenous MHC class I processing pathway.

Although the recognition of a foreign protein in the context of the MHC class I molecule may be sufficient for the recognition and destruction of affected target cells by CTLs, the induction of antigen-specific CTLs from T-lymphocyte precursors requires additional signals. Specialized antigen presenting cells (APCs) can provide both the antigen-MHC class I ligand and the accessory signals required in the induction phase of CTL-mediated immunity. General properties of APCs include MHC class I and class II expression, expression of various adhesion molecules important for APC-lymphocyte interaction, and expression of costimulatory molecules such as CD80 and CD86. Examples of APCs include macrophages and dendritic cells (including cutaneous epidermal Langerhans cells, dermal dendritic cells, and dendritic cells resident in lymph nodes and spleen).

Attempts to induce antigen-specific CTL responses in vivo by immunization with killed tumor cells, killed virus-infected cells, or component proteins have generally been unsuccessful, presumably because proteins in the extracellular fluids cannot enter the cytosol and access the MHC class I presentation pathway.

Mayordomo, et al., 1995, *Nature Med.* 1(12): 1297–1302 disclose in vitro culture of peptide-pulsed dendritic cells, which show protection against the associated tumor challenge. The authors state that dendritic cells cultured in the presence of GM-CSF+IL-4 and transfected with chicken ovalbumin (OVA) were capable of preventing establishment of an $OVA^+$ tumor, but not the untransfected parental melanoma.

Porgador and Giboa, 1995, *J. Exp. Med.* 182: 255–260 discloses use of dendritic cells to induce CTLs. No tumor challenge data is presented and no mention of CTL-mediated cross-priming with a peptide antigen is presented.

Nabel and coworkers (1995, *Annals of the NY Academy of Sciences* 772: 227–31; *Human Gene Therapy*, 1994, 5(1):57–77; *Proc. Natl. Acad. Sci.*, 1993, 90:11307–11311) disclose a method of cancer immunotherapy whereby a known tumor antigen is delivered to tumor cells in vivo to stimulate cell-mediated immunity against tumor growth. The authors do not disclose immunization with a generic artificial target antigen to achieve cross-priming either in vitro or in vivo.

Boon, 1992, *Advances in Cancer Research* 58:177–210, reviews the field of tumor rejection antigens as it stood in 1992. The author offers a perspective in regard to the use of tumor rejection antigens regarding methods of tumor immunization. However, the author does not suggest or teach immunization with a generic artificial target antigen to achieve cross-priming either in vitro or in vivo.

Wahl, et al., 1995, *J. Immunotherapy with Emphasis on Tumor Immunology* 17(1): 1–11, show increased enhanced generation of therapeutic T-cells in response to transfection of MHC class I gene H-2Ks to a poorly immunogenic tumor cell line. The authors do not address immunization by a generic artificial target antigen to achieve cross-priming either in vitro or in vivo.

Sato, et al., 1995, *Clinical Immunology & Immunopathology*, 74(1):35–43, studied the immune response to dinitrophenyl-modified tumor cells. The authors detected an inflammatory response to patient immunization with these modified cells along with tumor regression. Again, the authors do not address immunization by a generic artificial target antigen.

Flamand, et al., 1994, *Eur. J. Immunol.* 24: 605–610 disclose in vitro culture of dendritic cells, pulsed with a peptide antigen, and subsequent induction of a T-cell dependent humoral response to the B cell tumor BCL1. No mention of cross-priming with ATA targeted CTLs is taught or suggested.

Williams, et al. (1991, *Proc. Natl. Acad. Sci. USA* 88: 2726–2730) showed the expression of the protein luciferase in intact epidermal cells following biolistic (biobalistic) delivery of the firefly luciferase gene.

Tang, et al. (1992, *Nature* 356: 152–154) utilized a biolistic (biobalistic) device to produce a humoral response to a foreign protein. A gene encoding hGH under control of either the CMV promoter or the β-actin promoter was delivered to the epidermal tissue of mice. Anti-hGH antibodies were detected in mice in response to this immunization procedure.

Fynan, et al. (1993, *Proc. Natl. Acad. Sci. USA* 90: 11478–11482) confirmed the findings of Tang, et al. by using a plasmid DNA construct encoding an influenza virus hemagglutinin glycoprotein. Fynan, et al. compared humoral responses generated by gene gun delivery of DNA coated gold beads to the epidermis with other mechanisms and found that the use of a biolistic (biobalistic) device 1) resulted in 95% protection to a lethal influenza challenge, 2) was the most efficient route for DNA immunization, proving to be substantially more effective than mucosal, intramuscular, or intravenous administration, and, 3) required 250 to 2500 times less DNA than saline inoculations. Direct targeting of APC cells for genetic immunization is not disclosed or suggested by Fynan, et al.

Liu and colleagues (Montgomery et al., 1993, *DNA Cell Biol.* 12:777–783; Ulmer et al., 1993, *Science.* 259:1745–1749; Donnelly et al., 1995, Nature Medicine 1:583–587) have demonstrated that untargeted, nonspecific intramuscular injection of naked DNA induces antigen-specific CTL responses to viral proteins and protective immunity to viral challenge.

Sun, et al. (1995, *Proc. Natl. Acad. Sci. USA* 92: 2889–2893) utilized a biolistic (biobalistic) device to produce an anti-tumor response in mice. The authors delivered a plasmid construct expressing IL-6 directly to a tumor site in mice. Expression of IL-6 afforded a form of cytokine gene therapy nonspecifically directed at the tumor.

Kundig et al. (1995, *Science.* 268:1343–1346) demonstrate that protein antigen localization to the lymphoid organs is critical for the induction of antigen-specific CTL responses in vivo.

Kovacsovics-Bankowski and Rock (1995, *Science* 267: 243–246) demonstrate a phagosome-to-cytosol pathway for protein antigens not normally presented through the MHC class I endogenous pathway. The authors speculate that proteins in particulate form internalized within phagosomes are in fact able to enter the cytosolic pathway for MHC class I presentation.

Despite the efforts documented in the above reference material, there remains a need to develop a cancer immunotherapy procedure which stimulates protective and therapeutic immunity to a wide variety of tumor types. The present invention both addresses and meets this need.

3. SUMMARY OF THE INVENTION

The present invention relates to methods of cancer immunotherapy. Although some tumor antigens are known, it is currently not feasible to identify relevant tumor antigens for each specific tumor and for each specific patient. The present invention obviates the requirement of having to characterize, isolate and reintroduce a specific tumor antigen in order to stimulate antigen specific CTL production and subsequent destruction of affected cells such as neoplastic cells and virally infected cells.

The present invention overcomes this obstacle by disclosing methods of anti-tumor immunization whereby a mammalian host is directly immunized with an artificial target antigen in a manner promoting a CTL-mediated immune response. Either prior, simultaneously, or subsequent to this primary immunization the tumor is resected from the mammalian host and tumor cells are cultured in vitro. These in vitro cultured tumor cells are engineered to present the artificial target antigen on the cell surface. A population of the engineered tumor cells are then inactivated or killed and introduced back into the patient as a secondary immunization. The end result of this cross-priming to natural MHC class I restricted tumor antigens is a tagging of the tumor cells with a potent artificial target antigen. These tagged, or engineered, tumor cells focus the immune response on host tumor cells in a manner sufficient to stimulate CTL-mediated immunity to multiple, additional undefined natural tumor antigens present on the unmodified host tumor cell surface.

The present invention also relates to methods of treating a viral infection through immunotherapy. It will be difficult and cumbersome to isolate, characterize and match an immunogenic viral antigen with the specific infectious virus in order to promote a cell-mediated immune response. Therefore, the present invention also discloses cross-priming immunization methods to treat a viral infection. This method involves loading the patient's virally infected cell population with a selected artificial target antigen (e.g., OVA) in combination with a primary immunization with this artificial target antigen. As an example, and not a limitation, cross priming to treat an HIV-infected patient would be possible. CD4$^+$ cells removed from the patient may be cultured, loaded with an artificial target antigen, such as OVA, and introduced back into the patient simultaneously or subsequent to a primary immunization of the patient with OVA. This particular example for treating viral infection negates the requirement of having to isolate, characterize, and reintroduce a specific HIV viral antigen (which must initially be shown to be immunogenic) in order to stimulate antigen specific CTL production and subsequent destruction of HIV-infected CD4$^+$ cells.

In the present invention it is preferable that the mammalian host be a human.

In the present invention it is preferable to utilize as an artificial target antigen a protein or protein fragment which is highly immunogenic and is characterized as 1) a tumor rejection antigen or an antigenic protein fragment; 2) a viral antigen or an antigenic protein fragment; or 3) any additional antigenic foreign protein or protein fragment. Examples of human TRAs which may be utilized in the present invention include but are not limited to MAGE-1, MAGE 3, Melan-A, gp100, p53, CEA and HER2/neu. Examples of viral antigens which may be utilized in the present invention include but are not limited to HIV gp120, HIV gp160, Influenza virus nucleoprotein and Hepatitis B surface antigen. Examples of additional foreign proteins include but are not limited to ovalbumin (OVA) and keyhole limpit hemocyanin (KLH).

Regarding the above-identified ATAs, since a tumor rejection antigen or viral antigen are not fundamentally different from any other protein synthesized by the cell, except that the host is intolerant to them, virtually any foreign protein that is capable of presentation on a cell surface through the MHC class I and elicits an immune response will be a potential candidate for use as an artificial target antigen. It is preferred to utilize the ovalbumin protein, the use of which is disclosed and exemplified throughout the specification. Additionally, it will be within the purview of the skilled artisan, in light of the teachings forwarded in this specification, to test additional proteins or protein fragments as a potential artificial target antigen to practice the claimed invention.

It is especially preferred to select a protein or protein fragment for use as an ATA to which most human patients have at one time or another generated a primary immune response. Examples include but are not limited to chicken ovalbumin and the Influenza virus nucleoprotein.

The patient is subjected to a primary immunization with the artificial target antigen in a manner promoting presentation of the antigen to the MHC class I pathway. It is preferable in practicing the present invention to present the ATA of choice either by (1) particulate antigen delivery; (2) peptide pulsing; or, (3) polynucleotide delivery. These three procedures insure optimum opportunity for the antigen to be presented to the MHC class I pathway and subsequently presented to the cell surface of the target tumor cell.

The patient is also subjected to a secondary immunization wherein tumor cells are engineered to present the ATA through the MHC class I pathway and subsequently present an immunogenic fragment on the tumor cell surface. First, it is preferable to resect the primary tumor from the patient and culture these tumor cells in vitro to generate a source of target tumor cells. It is again preferable to transfect the cultured tumor cells with a nucleotide sequence which expresses the artificial target antigen of interest. These transfected tumor cells will express the ATA at effective amounts for presentation and entry into the MHC class I pathway and subsequent presentation on the transfected tumor cell surface. These transfected tumor cells are killed or inactivated by known techniques prior to a secondary immunization. Alternatively, the cultured tumor cells may be pulsed with appropriate ATA peptide or protein antigen prior to the secondary immunization.

One embodiment of the present invention relates to a method of anti-tumor immunization wherein a human patient is first immunized with an ATA to promote a CTL-mediated response. The tumor is resected from the human patient and a population of tumor cells retrieved from the patient's tumor are cultured in vitro. The population of in vitro cultured tumor cells are transfected with a nucleic acid construction expressing the gene product presented to the MHC class I pathway for presentation of the ATA on the transfected tumor cell surface. These transfected tumor cells are killed or inactivated and utilized for the secondary immunization of the patient. Alternatively, cultured tumor cells may be loaded by pulsing with appropriate ATA peptide or protein antigen prior to the secondary immunization.

A specific embodiment of the present invention utilizes chicken ovalbumin as the ATA.

A preferred embodiment of the present invention in regard to utilizing chicken ovalbumin involves a primary immunization of the patient by particulate antigen delivery of OVA.

Another preferred embodiment of the present invention in regard to utilizing chicken ovalbumin involves (1) a primary immunization of the patient by particulate antigen delivery of OVA, and (2) transfecting cultured tumor cells with a DNA vector expressing chicken ovalbumin to promote optimal presentation of the chicken ovalbumin ATA to the MHC class I pathway.

Another specific embodiment of the present invention utilizes Influenza virus nucleoprotein as the ATA.

A preferred embodiment of the present invention in regard to utilizing Influenza virus nucleoprotein involves a primary immunization of the patient by particulate antigen delivery of Influenza virus nucleoprotein.

Another preferred embodiment of the present invention in regard to utilizing Influenza virus nucleoprotein involves (1) a primary immunization of the patient by particulate antigen delivery of Influenza virus nucleoprotein-Fe beads, and (2) transfecting cultured tumor cells with a DNA vector expressing the Influenza virus nucleoprotein to promote optimal presentation of this ATA to the MHC class I pathway.

For the sake of clarity the direct immunization of the patient with an ATA is referred to as the primary immunization while immunization with cultured tumor cells engineered to present the ATA at the cell surface is referred to as the secondary immunization. However, it will be evident upon review of the specification that these secondary immunizations may also take place either simultaneously to or preceding the primary immunization.

It will also be within the purview of the skilled artisan to perform in vivo targeting of the ATA to tumor cells. This strategy circumvents the need for a secondary immunization and may be useful in situations where the primary tumor is inaccessible or a where a metastases is targeted, including but not limited to a tumor metastasizing to the lung.

It will be known to the skilled artisan that proteins and nucleic acids can be precipitated onto particulates composed of a variety of materials including but not limited to gold, iron, and synthetic plastics.

It will also be known to the skilled artisan that various recombinant vectors may be used to generate an ATA transgene sequence to be delivered to cultured tumor cells. The preferred vector, due primarily to ease of handling, is a DNA plasmid vector.

It is an object of the present invention to provide therapeutic or prophylactic genetic immunization against neoplastic cells.

It is an object of the present invention to provide a method for anti-tumor immunization procedures wherein no requirement exists for characterization of one or more tumor rejection antigens for each specific tumor and for each specific patient.

It is an object of the present invention to provide a method of anti-tumor immunization whereby a mammalian host is subjected to a primary immunization with an artificial target antigen and a secondary immunization with killed or inactivated ATA-engineered tumor cells in such a manner sufficient to stimulate CTL-mediated immunity to multiple, additional undefined natural tumor antigens present on the unmodified tumor cell surface.

| 3.1 DEFINITIONS | |
|---|---|
| CTL | cytotoxic T lymphocyte |
| ATA | artificial target antigen |
| OVA | ovalbumin |
| DC | dendritic cells |
| APC | antigen presenting cell |
| NP | Influenza viral nucleoprotein |
| PBS | phosphate buffered saline |
| KLH | keyhold limpit hemocyanin |

4. BRIEF DESCRIPTION OF THE FIGURES

Figure 1B:
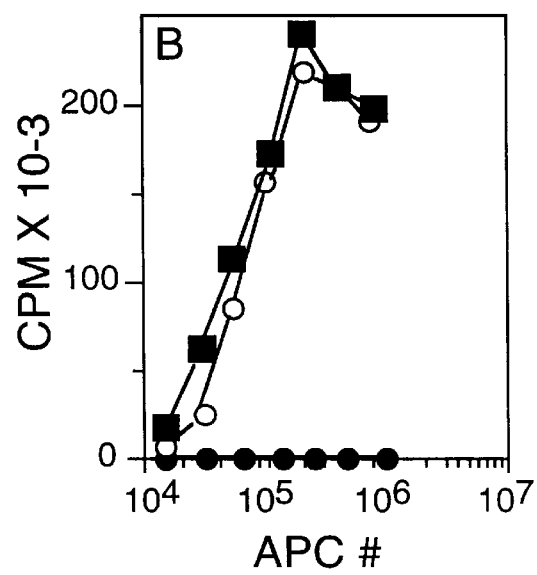

FIG. 1 shows functional presentation of ovalbumin by the transfected tumor cell lines MO4 and EG7. Microcultures were prepared with the T-cell hybridoma RF33.70 (anti-OVA+$K^b$) and the indicated number of transfected filled (squares) or untransfected (circles) tumor cells in the presence (open circles) or absence (filled circles) of added exogenous OVA-peptide SIINFEKL (10 ng/ml) as described (Rock, et al., 1990, *J. Immunol.* 45:804–811). After 18 hrs incubation, supernatants were harvested and assayed for IL-2 using the indicator cell line HT2 (Rock, et al., 1990, *J. Immunol.* 145: 804–811). (A) B16 and the OVA-transfected subclone MO4. (B) EL4 and the OVA transfected EL4 subclone EG7. OVA presentation by the OVA-transfected tumors was not significantly enhanced by the presence of exogenous SIINFEKL in the assay cultures.

Figure 2A:
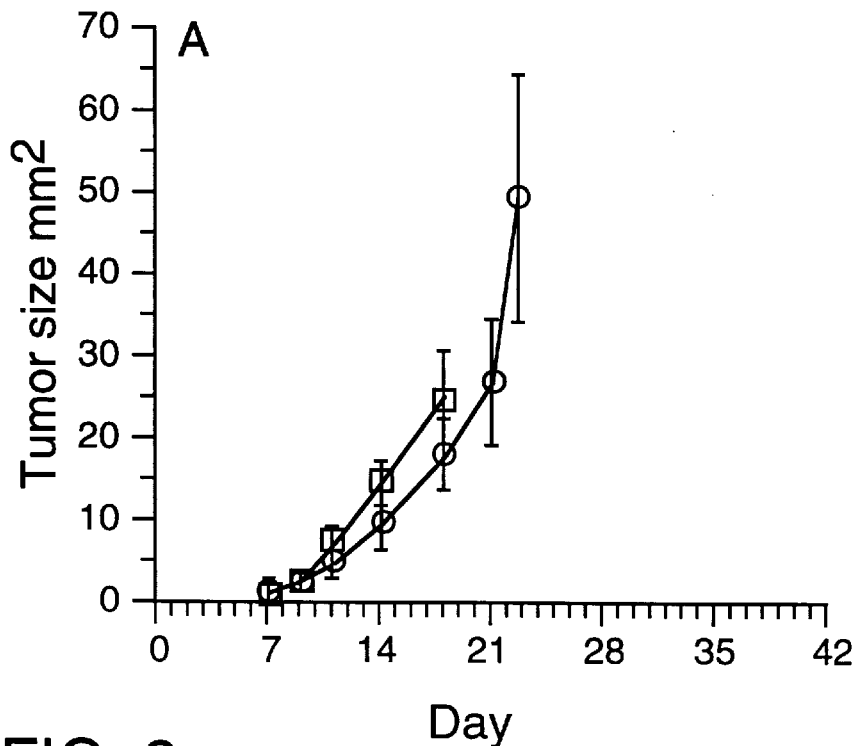
Figure 2B:
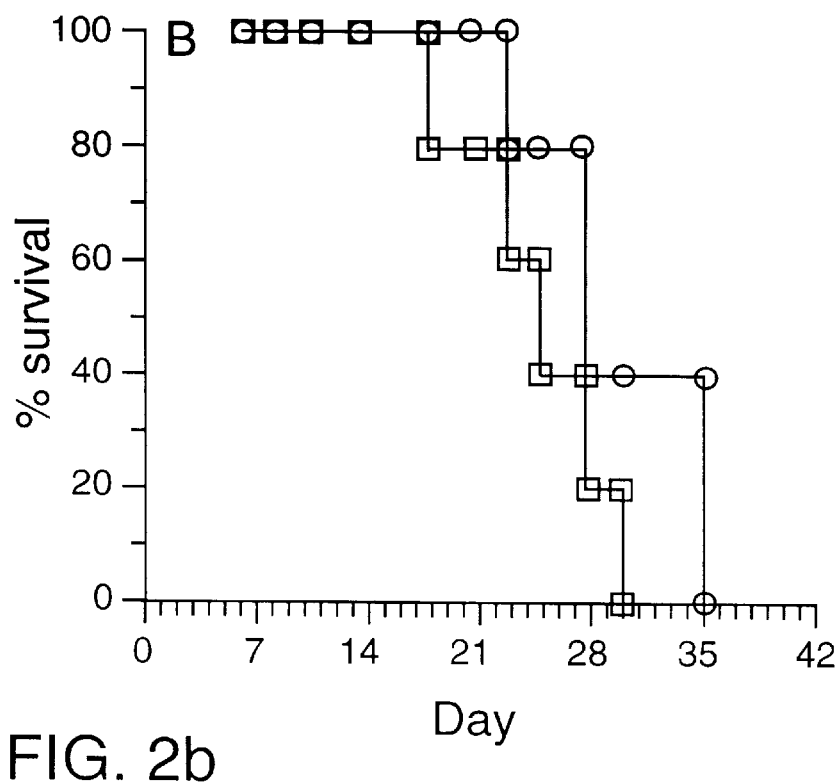

FIG. 2 shows that OVA expression by the B16 derived melanoma MO4 does not significantly effect in vivo tumor growth or host survival following tumor challenge. Mice were challenged with MO4 (circles) or B16 (squares) ($5 \times 10^4$/mouse, i.d., bilateral, mid-flanks). Tumor size (FIG. 2A) was assessed 3×/week and is reported as the average tumor area in square millimeters until the first death occurred in each group. Survival (FIG. 2B) is recorded as the percentage of surviving animals. All experiments included 5 mice/group and were repeated at least three times. Mice becoming moribund were sacrificed.

FIG. 3 shows that immunization with OVA-Fe beads induces CTLs that lyse OVA-transfected melanoma cells. C57BL/6 mice were immunized subcutaneously in the lower flanks with OVA-Fe beads (75 μg) (A) or soluble OVA (75 μg) (B). Subsequently, splenocytes were restimulated in vitro with irradiated MO4 melanoma cells and assayed for cytotoxic function using $^{51}$Cr-labelled B16 melanoma (open squares) or OVA-transfected MO4 melanoma targets (filled squares). Results are reported as percent specific $^{51}$Cr release at varying effector:target ratios. Data shown are the mean of triplicate cultures. The s.e.m. of triplicate counts was always less than 15% of the mean.

FIG. 4 shows that immunization with OVA-Fe beads induces protective and antigen-specific immunity to the OVA-transfected melanoma MO4. C57BL/6 mice were immunized subcutaneously in the lower flanks with OVA-Fe beads (75 μg)(open squares), an equivalent quantity of unconjugated Fe-beads (open triangles), or soluble OVA (75 μg)(filled triangles). Seven days later (day 0) immunized and non-immunized (filled squares) animals were challenged with $1\times10^5$ MO4 (A, C, and D) or B16 (B and E) melanoma cells. The size (A and B) of each tumor was assessed at least twice weekly and is reported as the average tumor area±s.e.m. in square millimeters. Survival (C, D and E) was recorded as the percentage of surviving animals. All experiments included five mice per group and were repeated at least three times. Mice that became moribund were killed.

Figure 5:
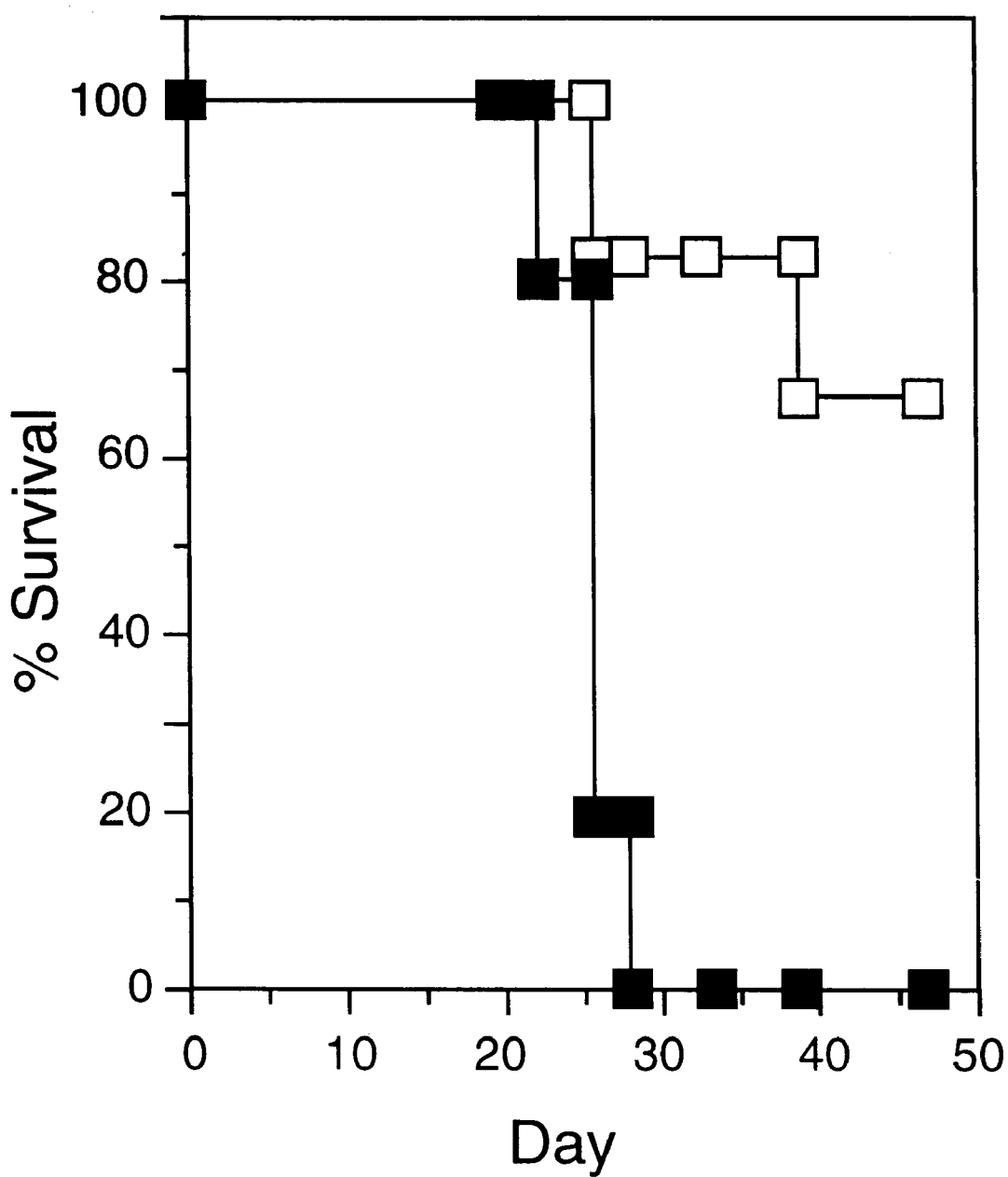

FIG. 5 shows that immunization with particulate OVA and challenge with MO4 induces long-lasting protective immunity to B16 melanoma. Five naive mice (filled squares) and six surviving mice (open squares) that had been immunized with OVA-Fe beads and challenged with MO4 as described (FIG. 4) were challenged with the parental melanoma B16. The six surviving mice were pooled from three separate experiments and had survived at least 65 days from initial tumor challenge. The percentage of surviving animals was recorded from the time of B16 challenge (day 0).

FIG. 6 shows immunization with peptide-pulsed DC induces protective immunity to lethal tumor challenge. C57BL/6 mice were immunized twice with PBS (open squares), peptide-pulsed DC (solid squares), peptide+β2M (open triangles), or DC alone (solid triangles) on days 0 and 7. Mice were challenged with MO5 7 d after the last immunization ($5\times10^4$ cells/mouse, i.d., bilateral midflanks) (day 0). Tumor size (A and B) was assessed three times per week and is reported as the average tumor area in square millimeters until the first death occurred in each group. Survival (C and D) is recorded as the percentage of surviving animals. All experiments included five mice per group. Mice becoming moribund were killed.

FIG. 7 shows that tumor immunity induced by peptide-pulsed DC is antigen specific and CTL mediated. C57BL/6 mice were immunized twice with PBS (open symbols) or peptide-pulsed DC (solid symbols) on days 0 and 7. Some mice were depleted of CD8 T lymphocytes by i.p. injection of anti-CD8 mAb 7 and 9 d after the last immunization (C and F). Mice were challenged with MO5 (A, C, D, and F) or B16 (B and E) as described (FIG. 6) 10 d after the last immunization (day 0). Tumor size (A-C) and survival (D-F) were recorded as described (FIG. 6). All experiments included five mice per group and were repeated at least three times. Mice becoming moribund were killed.

Figure 8:
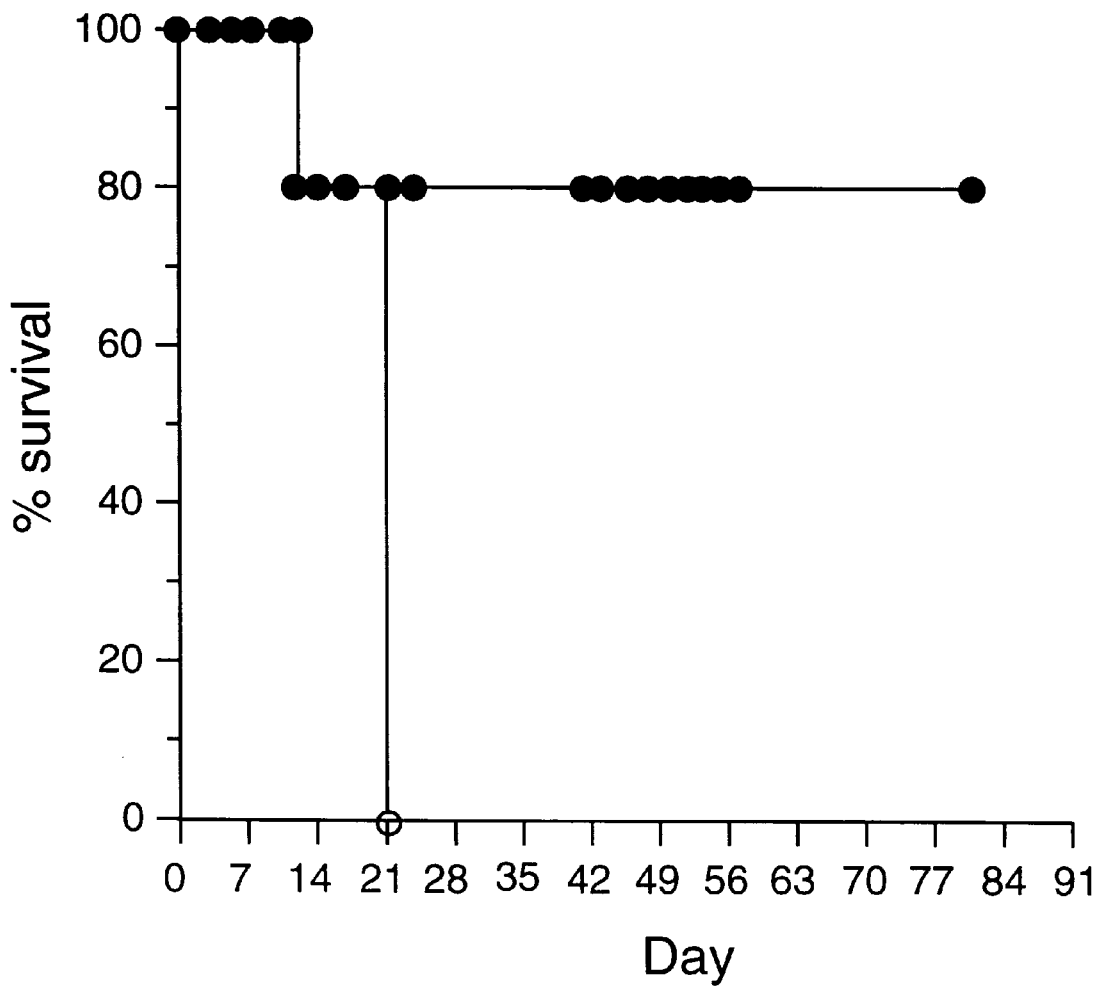

FIG. 8 shows that immunization with peptide-pulsed DC and challenge with MO5 induces long-lasting protective immunity to B16. Naive mice (open circles) and surviving mice that had been immunized with peptide-pulsed DC (46 d previously) and challenged (solid circles) as described (FIG. 6,7) were rechallenged with the parental B16 melanoma ($5\times10^4$ cells/mouse, i.d. bilateral, midflanks)(day 0). Survival is recorded as described (FIG. 6). Each group contained five mice. Experiments were repeated three times, and a representative experiment is shown. Mice that appeared moribund were killed.

5. DETAILED DESCRIPTION OF THE INVENTION

The present invention relates to methods of cancer immunotherapy. Although some tumor antigens are known, it is currently not feasible to identify relevant tumor antigens for each specific tumor and for each specific patient. The present invention obviates the requirement of having to characterize, isolate and reintroduce a specific tumor antigen in order to stimulate antigen specific CTL production and subsequent destruction of affected cells such as neoplastic cells and virally infected cells.

The present invention overcomes this obstacle by disclosing methods of anti-tumor immunization whereby a mammalian host is directly immunized with an artificial target antigen in a manner promoting a CTL-mediated immune response. Either prior or subsequent to this primary immunization the tumor is resected from the mammalian host and tumor cells are cultured in vitro. These in vitro cultured tumor cells are engineered to present the artificial target antigen on the cell surface. A population of the engineered tumor cells are then inactivated or killed and introduced back into the patient as a secondary immunization. The end result of this cross-priming to natural MHC class I restricted tumor antigens is a tagging of the tumor cells with a potent artificial target antigen. These tagged, or engineered, tumor cells focus the immune response on host tumor cells in a manner sufficient to stimulate CTL-mediated immunity to multiple, additional undefined natural tumor antigens present on the unmodified host tumor cell surface.

The present invention also relates to methods of treating a viral infection through immunotherapy. It will be difficult and cumbersome to isolate, characterize and match an immunogenic viral antigen with the specific infectious virus in order to promote a cell-mediated immune response. Therefore, the present invention also discloses cross-priming immunization methods to treat a viral infection. This method involves loading the patients virally infected cell population with a selected artificial target antigen (e.g., OVA) in combination with a primary immunization with this artificial target antigen. As an example, and not a limitation, cross priming to treat an HIV-infected patient would be possible. CD4$^+$ cells removed from the patient may be cultured, loaded with an artificial target antigen, such as OVA, and introduced back into the patient simultaneously or subsequent to a primary immunization of the patient with OVA. This particular example for treating viral infection negates the requirement of having to isolate, characterize, and reintroduce a specific HIV viral antigen (which must initially be shown to be immunogenic) in order to stimulate antigen specific CTL production and subsequent destruction of HIV-infected CD4$^+$ cells.

An initial step is choosing the artificial target antigen (ATA) for use in practicing the present invention. Known tumor rejection antigens and viral antigens are not fundamentally different from host cell proteins except for the fact that they are by definition "foreign" and the host is not tolerant to their presence. Therefore, a marked advantage of the disclosed method of anti-tumor immunization is that virtually any foreign protein capable of entering the MHC class I pathway to present an antigenic peptide fragment on a tumor cell surface is a candidate for potential use as an ATA. The skilled artisan will face a plethora of choices for a protein or protein fragment to use as an ATA in practicing the present invention.

One consideration that may prompt use of a certain foreign antigen for use as an ATA will be the patients past medical history. For example, most individuals will have in the past been exposed to specific foreign antigens from which a primary immune response ensued. Two natural choices are chicken egg ovalbumin (present in vaccination cocktails) and the Influenza virus nucleoprotein (associated with the common flu). Most individuals will have been exposed to either or both antigen and each is known to be highly immunogenic.

It is also preferable to use other highly immunogenic proteins or protein fragments as an ATA. Examples of such classes of peptides include but are not necessarily limited to 1) a tumor rejection antigen or an antigenic protein fragment; 2) a viral antigen or an antigenic protein fragment; or 3) any additional antigenic foreign protein or protein fragment. Examples of human TRAs which may be utilized in the present invention include but are not limited to MAGE-1, MAGE 3, Melan-A, gp100, p53, CEA and HER2/neu. Examples of viral antigens which may be utilized in the present invention include but are not limited to HIV gp120, HIV gp160, Influenza virus nucleoprotein and Hepatitis B surface antigen. Examples of additional foreign proteins include but are not limited to ovalbumin (OVA) and keyhole limpit hemocyanin (KLH).

The ATA of choice must then be administered to the host in a primary immunization in a manner which promotes presentation of the ATA through the MHC class I pathway of a host antigen presenting cell (APC). It is preferable in practicing the present invention to present the ATA of choice either by (1) particulate antigen delivery, (2) peptide pulsing, or (3) particulate polynucleotide delivery. These three procedures insure optimum opportunity for the antigen to be presented to the MHC class I pathway and subsequently presented to the cell surface of the target tumor cell. However, any technique which accomplishes this goal may be utilized by the artisan in this primary immunization procedure.

Example Section 7 presents data showing that particulate antigen delivery is a preferred strategy for use in a primary immunization of the host. The OVA/B16 murine melanoma model (see Example Section 6) exemplifies particulate antigen delivery in primary immunization. The ATA is covalently coupled to a particulate composed of a material including but not limited to gold, iron, or synthetic plastics. In this case, OVA-Fe beads are used in a primary immunization of the host to target APCs, which will present OVA to the MHC class I pathway. Antigen presenting cells (APCs) provide both the antigen-MHC class I ligand and the accessory signals required in the induction phase of CTL-mediated immunity. General properties of APCs include MHC class I and class II expression, expression of various adhesion molecules important for APC-lymphocyte interaction, and expression of costimulatory molecules such as CD80 and CD86. Examples of APCs include macrophages and dendritic cells (including cutaneous epidermal Langerhans cells, dermal dendritic cells, and dendritic cells resident in lymph nodes and spleen).

This direct primary immunization with OVA-Fe beads protected mice from a local tumor challenge from MO4 cells as well as from death. This OVA-Fe induced immunity is dependent on $CD8^+$ cells. Therefore, a direct in vivo immunization approach using particulate antigen delivery successfully completes a stage of generating a CTL-mediated response to the engineered MO4 cells. More importantly, Example Section 7 shows that mice survive a subsequent challenge by the parental B16 tumor. This data shows that immunity is generated to other antigens shared and expressed by both the engineered tumor cell (MO4) and the parental (B16) tumor. Therefore, a preferred anti-tumor immunization protocol of the present invention relates to presenting a first known antigen, or ATA, to the host in particulate form so as to generate a first CTL-mediated response. This same or substantially same ATA is also presented to the host in the form of an engineered tumor cell in a secondary immunization such that an additional, sustained immune response will be generated against the remaining population of unmodified tumor cells. It will be known that a population of particulate antigens may be delivered to the host in any number of ways, including but not necessarily limited to subcutaneous injection, biolistic particle bombardment, and intravenous injection.

It will be evident that ex vivo based methods of targeting APCs, such as exemplified in Example Section 8 in conjunction with peptide-pulsing, may be utilized in the present invention in conjunction with particulate antigen delivery.

Example Section 8 presents data supporting an ex vivo approach of presenting the ATA to the appropriate cell type in a primary host immunization. The OVA/B16 murine melanoma model and the EG7 murine thymoma models were used to show that a primary immunization by peptide pulsing of in vitro cultured APCs, dendritic cells, with an ATA will promote induction of tumor-specific immune responses.

Dendritic cells are cultured in vitro, pulsed with an ATA (such as OVA), inactivated, and reintroduced back into the host. Example Section 8 shows that peptide pulsing of APCs with an artificial target antigen successfully completes a stage of generating a CTL-mediated response to the engineered MO4 (or EG7) cells as well as showing that mice survive a subsequent challenge by the parental B16 tumor. Therefore, another preferred anti-tumor immunization protocol of the present invention relates to presenting a first known antigen, or ATA, to the host via peptide pulsed APCs so as to generate a first CTL-mediated response which is essential to initiate the cascade of events which will follow a successful secondary immunization.

A third preferred option for use in the primary immunization phase of the present invention is delivery of polynucleotides to the host, including but not necessarily limited to subcutaneous injection, biolistic particle bombardment, particulate polynucleotide injection, intramuscular injection, lipid-mediated transfer or injection of a polynucleotide carried by a viral vector. In regard to this option, a DNA vector is constructed which encodes and will express the ATA of choice upon delivery to the target APC, such as dendritic cells or macrophages. It is within the purview of the skilled artisan to construct an appropriate DNA expression vector which expresses adequate levels of the ATA subsequent to delivery to the target cell. The polynucleotide may be targeted for either an in vivo or ex vivo delivery to the target APC. A preferred method of ex vivo delivery will involve utilizing cultured dendritic cells, as exemplified in Example Section 8 in relation to peptide-pulsing experiments.

The patient is also subjected to a secondary immunization wherein tumor cells are engineered to present the ATA to the MHC class I pathway and subsequently present an immunogenic fragment on the tumor cell surface. First, it is preferable to resect the primary tumor from the patient and culture these tumor cells in vitro to generate a source of target tumor cells. It is again preferable to transfect the cultured tumor cells with a nucleotide sequence which expresses the artificial target antigen of interest. These transfected tumor cells will express the ATA at effective amounts for presentation and entry into the MHC class I pathway and subsequent presentation to the transfected tumor cell surface. These transfected tumor cells are killed or inactivated by known techniques prior to a secondary immunization. Alternatively, the cultured tumor cells may be subjected to peptide pulsing prior to the secondary immunization.

For this purpose, human tumors can be excised by techniques available to the artisan of ordinary skill. Single cell suspensions can then be made from these tumors by limited enzymatic digestion of physical disruption using standard techniques. Single cell suspensions of tumors can be cultivated by techniques appropriate to the specific tumor and generally known to one of ordinary skill in the art.

Therefore, an embodiment of the present invention relates to a method of anti-tumor immunization wherein a human patient is subjected to a primary immunization with an ATA to promote a CTL-mediated response in combination with a secondary immunization comprising tumor resection, culturing tumor cells in vitro, transfecting the tumor cells with a nucleic acid construction expressing the ATA of interest, killing or inactivating the transfected tumor cells and immunizing the patient with the inactivated tumor cells.

A specific embodiment of the present invention utilizes chicken ovalbumin as the ATA in combination with the above-mentioned secondary immunization protocol dependent upon transfection of cultured tumor cells with a DNA vector expressing chicken ovalbumin.

A preferred embodiment of the present invention in regard to utilizing chicken ovalbumin involves a primary immunization of the patient by particulate antigen delivery of OVA-Fe beads in combination with the above-mentioned secondary immunization protocol dependent upon transfection of cultured tumor cells with a DNA vector expressing chicken ovalbumin.

Another specific embodiment of the present invention utilizes Influenza virus nucleoprotein as the ATA in combination with the above-mentioned secondary immunization protocol dependent upon transfection of cultured tumor cells with a DNA vector expressing chicken ovalbumin.

A preferred embodiment of the present invention in regard to utilizing Influenza virus nucleoprotein (NP) involves a primary immunization of the patient by particulate antigen delivery of NP-beads in combination with the above-mentioned secondary immunization protocol dependent upon transfection of cultured tumor cells with a DNA vector expressing NP.

It will also be within the purview of the skilled artisan to perform in vivo targeting of the ATA to tumor cells. This strategy circumvents the need for a secondary immunization and may be useful in situations where the primary tumor is inaccessible or a where a metastases is targeted, including but not limited to a sarcoma metastasizing to the lung.

It will also be known to the skilled artisan that various recombinant vectors may be used to generate an ATA transgene sequence to be applied delivered to cultured tumor cells. The preferred vector, due primarily to ease of handling, is a DNA plasmid vector.

6. EXAMPLE: OVA/B16 GENETIC MURINE TUMOR MODEL

The OVA/B16 murine model was used to generate the data disclosed in Example Section 7 and Example Section 8 which exemplify the claimed invention. The OVA/B16 murine system is attractive for several reasons: (1) the B16 melanoma is an extensively studied murine tumor, (2) in vivo growth characteristics and metastasis of this tumor line are well characterized, and (3) ovalbumin has a well defined structure. The intracellular processing and presentation of OVA in the C57B1/6 mouse is known. In particular the structure of the processed peptide, presented in association with MHC class I $K^b$, is known. Assays for the functional expression of ovalbumin peptide [SIINFEKL] in association with H2-$K^b$ using the T-T hybridoma 33.70.A1 anti-OVA-$K^b$ are also known (Kovacovics-Bankowski, et al., 1993, Proc. Natl. Acad. Sci. USA. 90: 4942–4946). Techniques to evaluate in vivo induction of OVA specific CTLs in this system are also well described (Moore, et al., 1988, Cell 54: 777–785).

The murine lymphoma cell line EL4 is a C57BL/6 T lymphoma and the cell line EG7 is a chicken egg ovalbumin (OVA)-transfected subclone of EL4. This additional OVA/murine tumor model system was used in Example Section 8 to exemplify the claimed invention.

Mice and Cell Lines. Female C57BL/6 mice, 5–8 weeks old were purchased from the Jackson Laboratories, Bar Harbor, Me. EL4 is a C57BL/6 T-lymphoma, and EG7 is a chicken egg ovalbumin (OVA)-transfected subclone of EL4 (Moore, et al. 1988, Cell 54: 777–785). The C57BL/6 derived murine melanoma B16 (Fidler, et al., 1976, Cancer Res. 36: 3160–3165) was obtained from American Tissue Type Collection (ATCC). MO4 was constructed by transfection of B16 with the pAc-Neo-OVA plasmid as described. (Falo, et al, 1995, Nature Med. 1: 649–653, Moore, et al. 1988, Cell 54: 777–785) Monoclonal antibodies were prepared from the hybridomas GK1.5 (anti-CD4, ATCC TIB-207), 2.43 (anti-CD8 antibodies was raised in Balb/c nu/nu mice by i.p. injection of GKf1.5 cells ($3 \times 10^6$) and IFA (0.5 ml/mouse).

After OVA transfection of the B16 melanoma, and selection, the transfected B16 melanoma subclone, MO4 was isolated. The parent melanoma B16, and the OVA transfectant express similar levels of functional $K^b$ on the cell surface as measured by presentation of OVA peptide (SIINFEKL) to RF33.70 (FIG. 1). In contrast, MO4/5, but not B16, is capable of hybridoma stimulation in the absence of exogenously added peptide (FIG. 1). This demonstrates endogenous production, processing, and presentation of the transfected antigen. Importantly, endogenous expression of OVA by MO4 did not significantly alter in vivo immunogenicity of the tumor (FIG. 2). Tumor growth (FIG. 2A) of B16 and MO4 is comparable in naive mice, as is host survival (FIG. 2B).

Figure 3A:
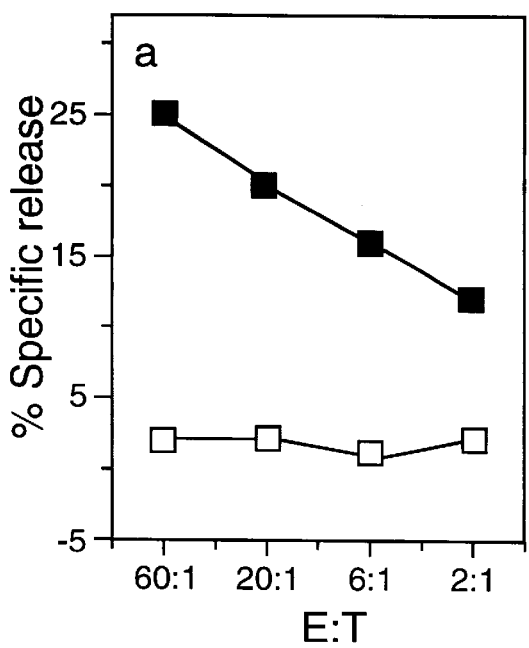
Figure 3B:
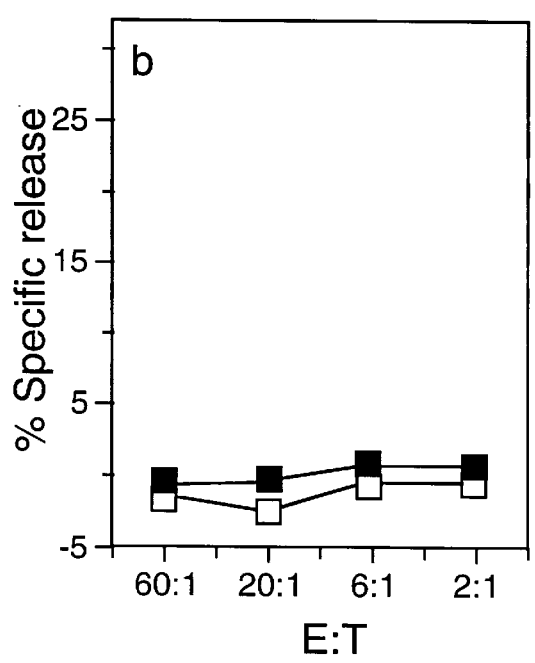
Figure 4A:
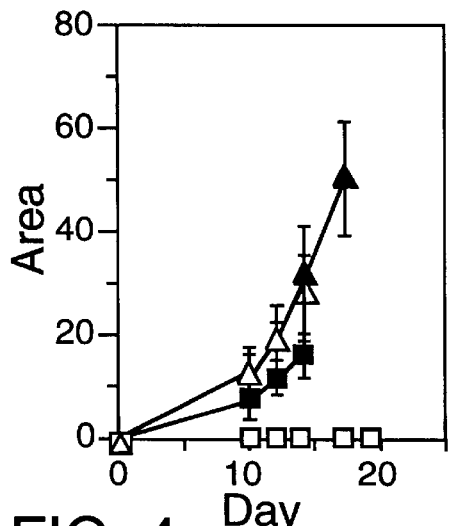
Figure 4B:
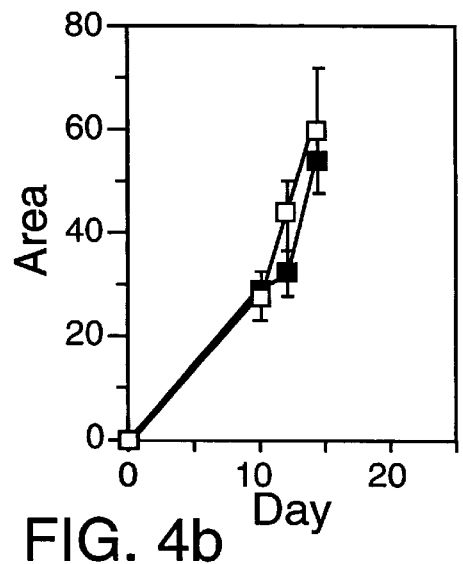
Figure 4C:
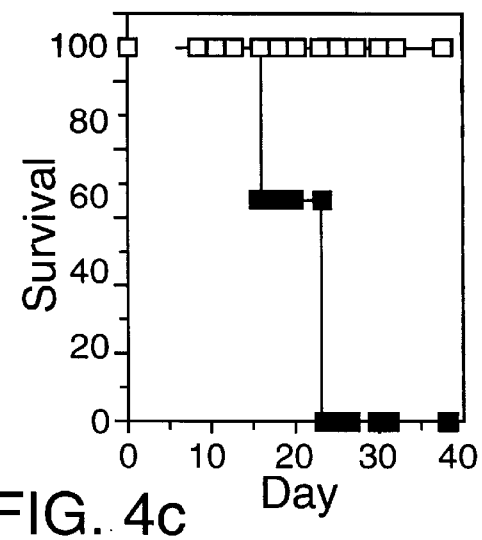
Figure 4D:
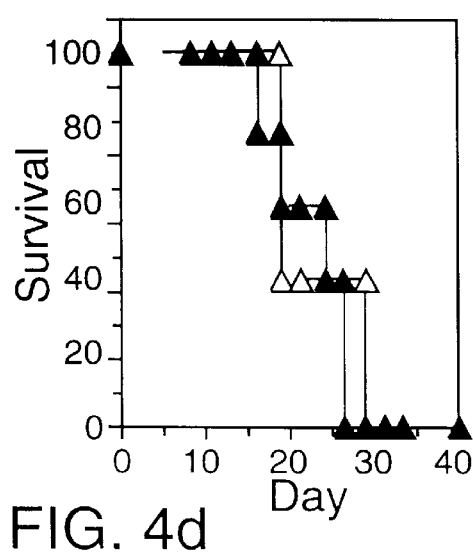
Figure 4E:
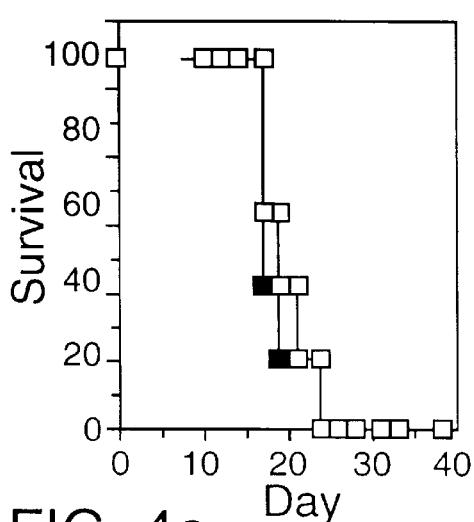

To evaluate the ability of particulate antigen to induce OVA-specific CTLs capable of killing the MO4 melanoma, C57BL/6 mice were immunized subcutaneously with ovalbumin conjugated to iron beads (OVA-Fe beads) without adjuvant. In vitro restimulated spleen cells from these mice specifically lysed the OVA-transfected melanoma MO4 but not the untransfected parent melanoma, B16 (FIG. 3A). In contrast, spleen cells from mice immunized with an identical quantity of soluble OVA failed to lyse either tumor target (FIG. 3B). The killing of tumor cells by CTL required immunization with the particulate form of OVA and expression of OVA by the tumor target. Primed CTL in vitro was detected fifteen weeks after immunization.

When MO4 cells are injected intradermally into C57BL/6 mice, tumors grow progressively, metastasize and kill the animals (FIG. 4A–E). The growth rate of MO4 cells in vivo is similar to that of untransfected B16 cells. Moreover, injection of even as few as $2 \times 10^4$ MO4 cells is lethal in >90% of the animals. Therefore, as for many tumor antigens, the expression of the ovalbumin antigen alone does not render this tumor sufficiently immunogenic to be rejected.

7. EXAMPLE: IMMUNIZATION AND IMMUNITY TO SHARED TUMOR ANTIGENS BY PARTICULATE PEPTIDE PRESENTATION AS THE PRIMARY IMMUNIZATION

The OVA/B16 murine melanoma model, as described in Example Section 6, was utilized to exemplify the claimed invention in this Example Section.

Antigenic constructs—Antigenic constructs used in this Example Section include chicken egg OVA (Sigma) dissolved in PBS, and the synthetic peptide $OVA_{257-264}$ in PBS. A particulate form of ovalbumin, OVA-Fe beads, was constructed by covalently coupling OVA to iron oxide (0.5–1.5 mm, Advanced Magnetics, Cambridge, Mass.) via an amino group as described by Kovascovics-Bankowski, 1995, *Proc. Natl. Acad. Sci. USA* 90: 4942–4946.

Cytotoxicity Assays—Splenocytes from immunized animals were restimulated with minor modifications of previously described protocols. Briefly, 1 week after immunization splenocytes ($30 \times 10^6$) were restimulated by coculture with irradiated (20,000 rad) MO4 melanoma cells ($10 \times 10^6$). Effector cells were harvested five days later and cultured with $2 \times 10^4$ $^{51}$Cr-labeled targets in round bottom microwells (200 µl) at the indicated effector target cell ratio. After 4 hours at 37° C., 100 µl of supernatant from triplicate microcultures was collected and counted and the percentage of specific release was calculated as described by Rock, et al. (1990, *J. Immunol.* 145: 804–811). Results are reported as the mean of triplicate cultures. The SEM of triplicate cultures was always less than 15% of the mean.

Protection Assays—C57BL/6 mice were immunized subcutaneously in both lower flanks with the indicated antigen. Seven days after the final immunization (day 0), OVA-immunized and non-immunized animals were challenged by intradermal injection in the mid-flanks bilaterally with melanoma cells ($1 \times 10^5$) at 2 times the dose lethal to 50% of the animals tested ($LD_{50}$). The size of each developing tumor was assessed at least twice weekly and recorded by measuring the largest perpendicular diameters, the product of which is referred to as the tumor area. Data reported as the average tumor area±s.e.m. in square millimeters. Survival was recorded as the percentage of surviving animals. Immunizations were administered in 50 µl and tumor challenges in 100 µl of PBS. Melanoma cells for injection were harvested by limited trypsinization and washed three times in PBS. Injected cells were more than 95% viable by trypan blue exclusion. All experiments included 5–10 mice per group (specified in the respective figure description in Section 4) and were repeated at least three times. Mice that became moribund were killed according to the animal care guidelines of the University of Pittsburgh Medical Center and the Dana Farber Cancer Institute. In some experiments, animals were depleted of $CD8^+$ cells. This was accomplished by intraperitoneal injection of CD8 mAb (2.43) 7 and 9 days after immunization as described followed by tumor challenge on day 10.

A first exemplification of the present invention is immunization of C57BL/6 mice with ovalbumin conjugated to iron beads (OVA-Fe beads). This method of primary immunization protected the mice from a tumor challenge from MO4 cells at >10 times the dose lethal to 50% of the animals tested. The mice were protected from tumor growth locally and from death as described in Example Section 6.

The OVA-Fe induced immunity was shown to be dependent on $CD8^+$ cells. The depletion of the subset of T cells by injections of anti-CD8 monoclonal antibody rendered the mice susceptible to an MO4 challenge.

This model was used to test the hypothesis that generating an immune response to a first antigen would promote immunity to other antigens shared and expressed by the tumor. FIG. 5 shows that immunization with OVA-Fe beads and challenge with MO4 induces long-lasting protective immunity to the parent B16 melanoma. Five naive mice and six surviving mice that had been immunized with OVA-Fe beads and challenged with MO4 were challenged with the parental melanoma B16. The six surviving mice were pooled from three separate experiments and had survived at least 65 days from initial tumor challenge. The percentage of surviving animals was recorded from the time of B16 challenge (day 0).

Therefore, this data exemplifies the essence of the present invention: a host vaccinated with a first antigen in a form sufficient to promote a CTL-mediated immune response will mediate an effective immune response to additional antigens presented on the cell surface of the target cell which has presented an antigenic peptide from the first antigen. Therefore, an opportune anti-tumor immunization protocol will be to present a known first antigen, or ATA, to both the host as a primary immunization and to at least a population of targeted tumor cells in a secondary immunization in such a way that an additional, sustained immune response will be generated against the remaining population of unmodified tumor cells.

8. EXAMPLE: IMMUNIZATION AND IMMUNITY TO SHARED TUMOR ANTIGENS BY PEPTIDE PULSING DENDRITIC CELLS AS THE PRIMARY IMMUNIZATION

Dendritic cells—Dendritic cells were prepared by depleting bone marrow cells of lymphocytes and culturing overnight in RPMI 1640 supplemented with 10%FCS, L-glutamine, antibiotics and 2-ME in 24 well plates at $10^6$ cells/well. Cells were replated on day 1 at $2.5 \times 10^5$ cells/well with GM-CSF ($10^3$ U/ml, Sigma, St. Louis, Mo.) and murine rIL-4 ($10^3$ U/ml, Genzyme, Cambridge, Mass.) and loosely adherent cells were harvested on day 8. By flow cytometric analysis, these dendritic cells expressed CD45, CD44, CD11b (Mac-1), CD18, CD80, cD86 and class I and class II MHC antigens. Dendritic cells were pulsed 2 hrs at 37° C. with or without OVA peptide (20 ng/ml)+β2-microglobin (β2-M, 10 µl/ml, human, Sigma) in reduced serum media (Optimen, Gibco, Grand Island, N.Y.). Cells were then washed extensively, resuspended in PBS and irradiated (2000 rad) before injection into naive mice. The indicated number of bone marrow derived dendritic APCs were cocultured with OVA-encoding particulate polynucleotides prepared as described in Example Section 7 (50 µl/ml/$10^6$ cells of 7 mg/ml particulates) using either Fe beads (closed squares) or gold beads (closed circles) as the particulate substrate or soluble OVA protein (2 mg/ml) (open squares) for 24 hrs., washed, and then the indicated number of APCs were co-cultured in microcultures with the T-cell hybridoma RF33.70 (anti-OVA+$K^b$). After 18 hrs incubation, supernatants were harvested and assayed for IL-2 using the indicator cell line HT2 (Rock, et al., 1990, *J. Immunol.* 145: 804–811).

Both the B16 murine melanoma model and the EG7 murine thymoma models were used to show that a primary immunization by peptide pulsing, particularly peptide pulsing of dendritic cells, with an ATA will promote induction of tumor-specific immune responses.

Antigenic, Antibodies and Antigenic Constructs—Antigenic constructs used in this Example Section include chicken egg OVA (Sigma) dissolved in PBS, and the synthetic peptide $OVA_{257-264}$ in PBS. This peptide was synthesized by the Peptide Synthesis Facility of the University of Pittsburgh Medical Center. mAbs were prepared from the hybridomas GK1.5 (anti-CD4, ATCC TIB-207), 2.43 (anti-CD8, ATCC TIB-210) or 30-H12 (anti-Thy 1.2, ATCC TIB-107). Ascites containing anti-CD8 antibodies were raised in BALB.c nu/nu mice by i.p. injection of GK1.5 cells ($3 \times 10^6$) and IFA (0.5 ml/mouse).

Cytotoxicity Assays—Splenocytes ($30 \times 10^6$) harvested from mice 7–10 days after the last immunization were restimulated by coculture with C-treated EG7 cells ($7 \times 10^6$) and effector cells were harvested five days later. Target cells were labeled in RPMI (10% FCS with $^{51}$Cr (100 $\mu$Ci; NEN, Boston, Mass.) for 18 hours at 37° C., washed extensively, and cocultured at $2 \times 10^4$ cells/well with effector cells (at the ratios given in the figures) in 96-well round-bottom microwells (200 $\mu$l) at the indicated effector target cell ratio. After 4 hours at 37° C., 100 $\mu$l of supernatant from triplicate microcultures was collected and counted and the percentage of specific release was calculated as described by Rock, et al. (1990, *J. Immunol.* 145: 804–811). Results are reported as the mean of triplicate cultures. The SEM of triplicate cultures was always less than 15% of the mean.

Protection Assays—Protection assays were carried out essentially as described in Example Section 7. Briefly, C57BL/6 mice were immunized subcutaneously in both lower flanks with either peptide-pulsed DC or nonpulsed DC ($3 \times 10^4$/100 $\mu$l/side), peptide+$\beta$2M, or PBS on day 0 and boosted on day 7. Seven to ten days after the final immunization (day 0), OVA-immunized and non-immunized animals were challenged by intradermal injection in the midflanks bilaterally with MO5 or B16 melanoma cells ($2.5 \times 10^4$/100 $\mu$l/side) in PBS. Injected cells were>95% viable as determined by trypan blue exclusion. The size of each developing tumor was assessed at least twice weekly and recorded by measuring the largest perpendicular diameters, the product of which is referred to as the tumor area. Data are reported as the average tumor are±s.e.m. in square millimeters. Survival was recorded as the percentage of surviving animals. Immunizations were administered in 50 $\mu$l and tumor challenges in 100 $\mu$l of PBS. Melanoma cells for injection were harvested by limited trypsinization and washed three times in PBS. Experiments included 5 mice per group and were repeated at least three times. Mice that became moribund were killed according to the animal care guidelines of the University of Pittsburgh Medical Center and the Dana Farber Cancer Institute. In some experiments, animals were depleted of CD8$^+$ cells. This was accomplished by intraperitoneal injection of ascites (1 mg/ml, 200 $\mu$l/mouse) 7 and 9 days after immunization.

OVA peptide-pulsed DC were capable of inducing CTLs which lyse the OVA-expressing melanoma or the OVA-expressing thymoma EG7 in vitro. In vitro restimulated spleen cells from mice lysed MO5, but not the untransfected parent melanoma B16. Similarly, these effector cells lysed the OVA-expressing thymoma EG7, but not the untransfected parent tumor EL4. Tumor cell lysis was antigen specific, depending on expression of OVA by the tumor target. Lysis was dependent on Thy1$^+$CD8$^+$ subsets characteristic of MHC Class I-restricted CTL effector cells.

Figure 6A:
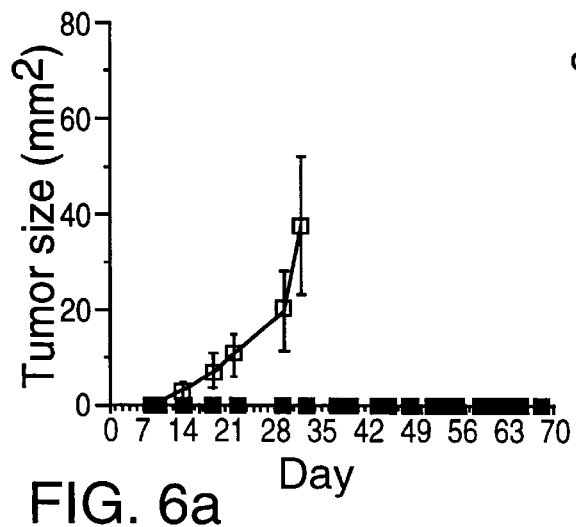
Figure 6B:
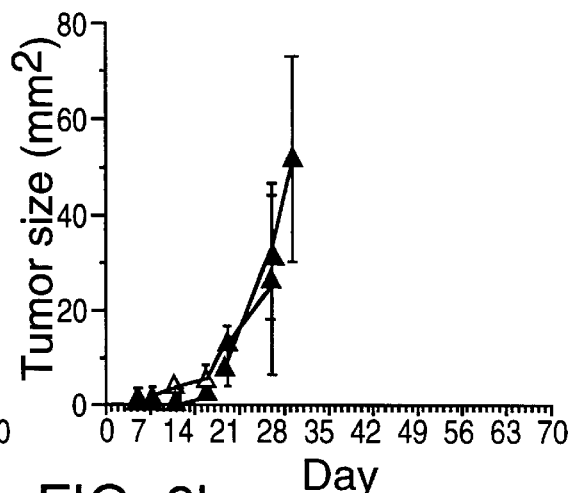
Figure 6C:
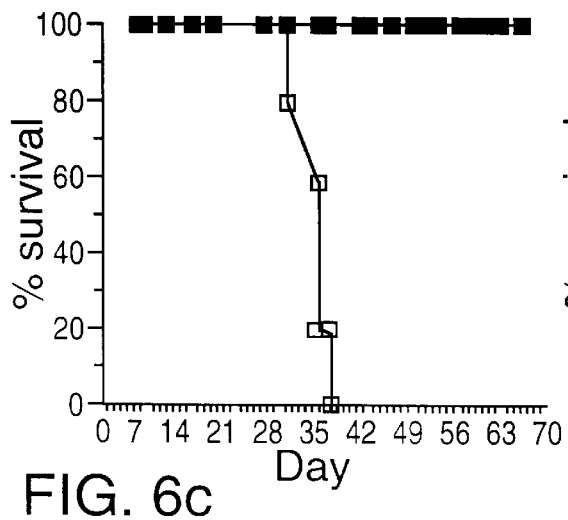
Figure 6D:
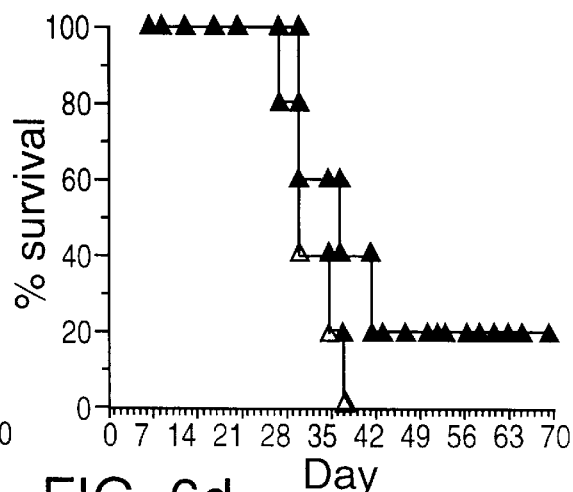
Figure 7A:
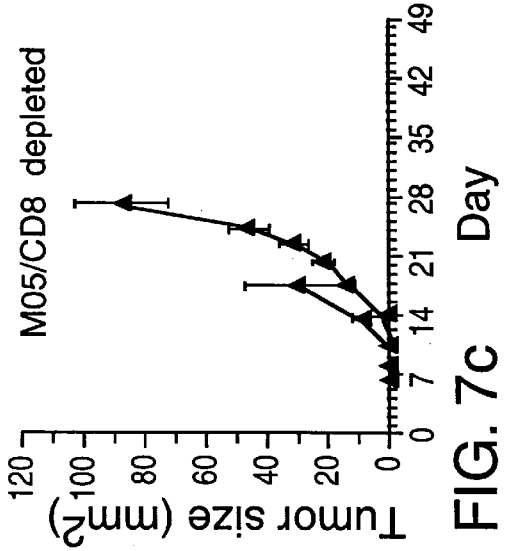
Figure 7B:
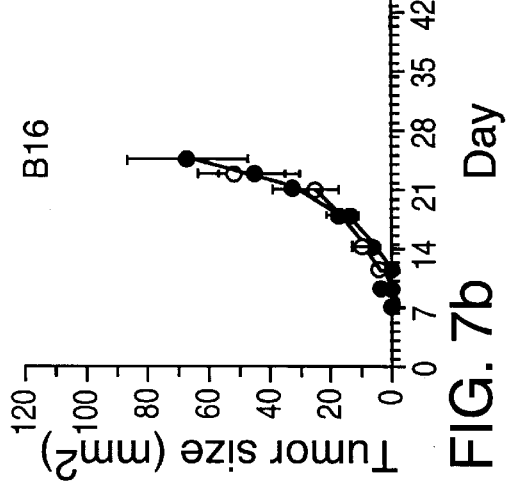
Figure 7C:
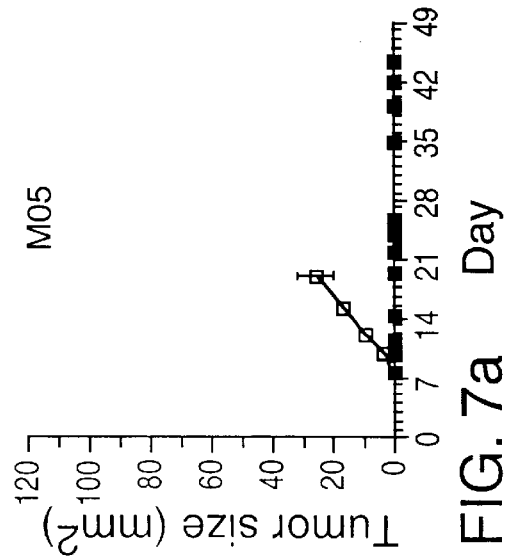
Figure 7D:
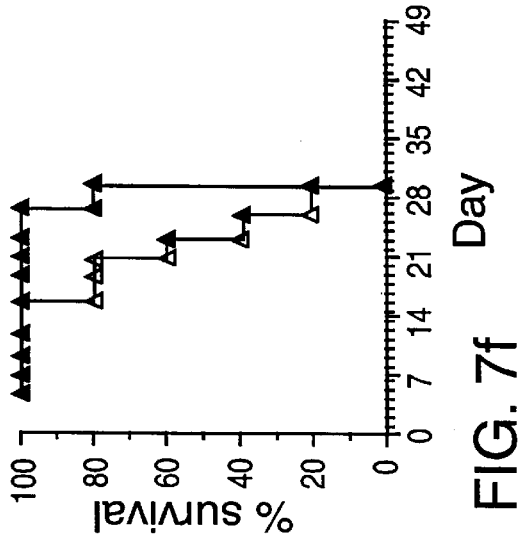
Figure 7E:
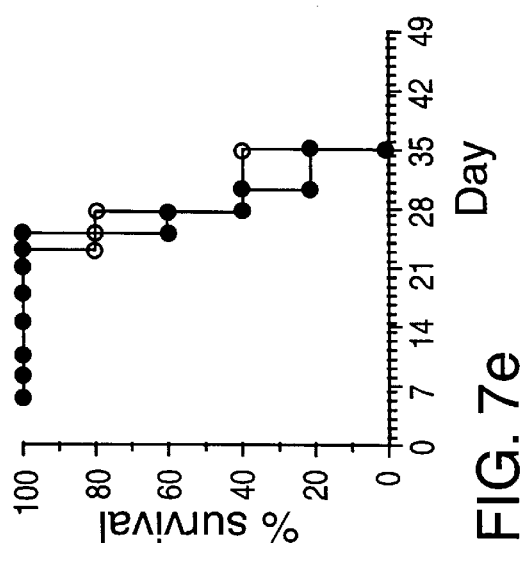
Figure 7F:
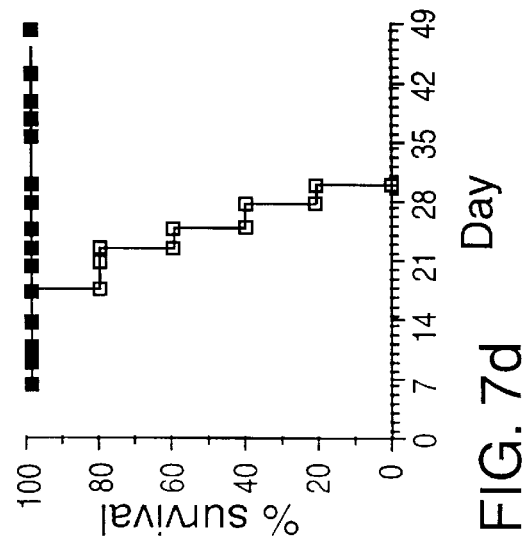

In light of the shown usefulness of these murine tumor models, groups of mice were subcutaneously immunized with SIINFEKL-pulsed DC, boosted 7 days later, and then challenged intradermally at a distant site with MO5 melanoma to determine the capacity of peptide-pulsed DC to induce protective tumor immunity. Immunized mice were protected from tumor growth locally (FIG. 6A) and from death (FIG. 6C). Tumors in control mice (PBS immunized) grew progressively (FIG. 6A) and were lethal (FIG. 6C). Mice immunized with DC not pulsed with SIINFEKL were not protected (FIG. 6B and 6D), suggesting that subcutaneously injected DC do not induce tumor immunity by antigen-independent mechanisms in this model. It is also unlikely that protection was the result of carryover of free SIINFEKL, as the peptide-pulsed DC were extensively washed before injection, and the peptide with $\beta$2M alone is not protective when injected subcutaneously without DC (FIG. 6B and 6D). Furthermore, mice immunized with SIINFEKL-pulsed DC were not protected from challenge with the untransfected parent B16 (FIG. 7B and FIG. 7E), indicating that protective immunity was antigen specific, depending on OVA expression by the tumor target. CD8$^+$ T cell contribution to protective tumor immunity by deleting groups of immunized or control animals of CD8$^+$ effector cells before tumor challenge by repeated i.p. injection of anti-CD8 mAB. Tumor growth and survival in immunized CD8$^+$ cell-depleted animals was similar to that observed in non-immunized controls, with or without T cell depletion (FIG. 7A, 7C, 7D and 7F). Therefore, CD8$^+$ T cells are essential for the protective tumor immunity induced by peptide-pulsed DC model in this model.

FIG. 8 shows that peptide-pulsed DCs may be utilized in the primary immunization of the present invention. Immunized mice that had rejected MO5 were protected from subsequent tumor challenge by the untransfected parent B16 (FIG. 8). Mice rejecting the OVA-transfected melanoma developed immunity to other antigens expressed on MO5 and "shared" with the untransfected parent melanoma. Immune responses to additional, undefined shared tumor antigens will augment antitumor immunity induced using defined antigens.

These examples show that immunotherapeutic responses may be generated initially by a primary immunization wherein the first antigen, or ATA, is delivered within the host in a manner which stimulates a CTL-mediated immune response dependent upon CD8$^+$ T cells.

Again, human tumors can be excised by techniques available to the artisan of ordinary skill. Single cell suspensions can then be made from these tumors by limited enzymatic digestion of physical disruption using standard techniques. Single cell suspensions of tumors can be cultivated by techniques appropriate to the specific tumor and generally known to one of ordinary skill in the art.

Whereas, particular embodiments of this invention have been described above for purposes of illustration, it will be evident to those persons of ordinary skill in the art that numerous variations of the details of the present invention may be made without departing from the invention as defined in the appended claims that follow.

What is claimed is:

1. A method of eliciting an immune response in a mammalian host capable of generating an immune response which comprises:
   a) immunizing firstly said mammalian host with a foreign artificial target antigen in a form promoting a CTL-mediated response;
   b) culturing in vitro a population of tumor cells;
   c) engineering said cultured tumor cells to include said foreign artificial target antigen within said cultured tumor cells such that said engineered cultured tumor cells promote presentation of said foreign artificial target antigen on the cell surface;
   d) inactivating said population of engineered cultured tumor cells;
   e) immunizing secondly said mammalian host with the inactivated population of said engineered cultured tumor cells;
   wherein an immune response against unmodified tumor cells is elicited as a result of said immunizing steps.

2. The method of claim 1 where said mammalian host is a human.

3. The method of claim 2 wherein said foreign artificial target antigen of step (a) is presented to said mammalian host as a particulate complex.

4. The method of claim 3 wherein said foreign artificial target antigen of step (c) is introduced to said cultured tumor cells by peptide pulsing.

5. The method of claim 3 wherein said foreign artificial target antigen of step (c) is introduced to said cultured tumor cells by transfection of a nucleic acid molecule expressing effective amounts of said foreign artificial target antigen.

6. The method of claim 2 wherein said foreign artificial target antigen of step (c) is introduced to said cultured tumor cells by transfection of a nucleic acid molecule expressing effective amounts of said foreign artificial target antigen.

7. The method of claim 2 wherein said foreign artificial target antigen of step (c) is introduced to said cultured tumor cells by peptide pulsing.

8. The method of claim 1 wherein said foreign artificial target antigen is a tumor antigen selected from the group consisting of Melan-A, p53, CEA, gp100, MAGE-1 and MAGE-2.

9. The method of claim 1 wherein said foreign artificial target antigen is a viral antigen selected from the group consisting of HIV gp120, HIV gp100, Influenza virus nucleoprotein and Hepatitis B surface antigen.

10. The method of claim 1 wherein said foreign artificial target antigen is an immunogenic foreign antigen selected from the group consisting of chicken ovalbumin and keyhole limpit hemocyanin.

11. The method of claim 1 wherein said foreign artificial target antigen is chicken ovalbumin.

12. A method of eliciting an immune response in a mammalian host capable of generating an immune response which comprises:
   a) culturing in vitro a population of tumor cells;
   b) engineering said cultured tumor cells to include a foreign artificial target antigen within said cultured tumor cells such that said engineered cultured tumor cells promote presentation of said foreign artificial target antigens on the cell surface;
   c) inactivating said population of engineered cultured tumor cells;
   d) immunizing said mammalian host first with an inactivated population of said engineered cultured tumor cells and second with said foreign artificial target antigen in a form promoting a CTL-mediated response;
   wherein an immune response against unmodified tumor cells is elicited as a result of said immunizing steps.

13. The method of claim 12 where said mammalian host is a human.

14. The method of claim 13 wherein said foreign artificial target antigen of step (d) is presented to said mammalian host as a particulate complex.

15. The method of claim 14 wherein said foreign artificial target antigen of step (b) is introduced to said cultured tumor cells by transfection of a nucleic acid molecule expressing effective amounts of said foreign artificial target antigen.

16. The method of claim 14 wherein said foreign artificial target antigen of step (b) is introduced to said cultured tumor cells by peptide pulsing.

17. The method of claim 13 wherein said foreign artificial target antigen of step (b) is introduced to said cultured tumor cells by transfection of a nucleic acid molecule expressing effective amounts of said foreign artificial target antigen.

18. The method of claim 13 wherein said foreign artificial target antigen of step (b) is introduced to said cultured tumor cells by peptide pulsing.

19. The method of claim 12 wherein said foreign artificial target antigen is a tumor antigen selected from the group consisting of Melan-A, p53, CEA, gp100, MAGE-1 and MAGE-2.

20. The method of claim 12 wherein said foreign artificial target antigen is a viral antigen selected from the group consisting of HIV gp120, HIV gp100, Influenza virus nucleoprotein and Hepatitis B surface antigen.

21. The method of claim 12 wherein said foreign artificial target antigen is an immunogenic foreign antigen selected from the group consisting of chicken ovalbumin and keyhole limpit hemocyanin.

22. The method of claim 12 wherein said foreign artificial target antigen is chicken ovalbumin.

* * * * *

UNITED STATES PATENT AND TRADEMARK OFFICE
CERTIFICATE OF CORRECTION

PATENT NO. : 5,951,975

DATED : September 14, 1999

INVENTOR(S) : Falo, Jr., et al.

It is certified that errors appear in the above-identified patent and that said Letters Patent should be corrected as shown below:

Col. 7, line 45 "(A " should read --(.4 --.

Col. 17, line 51 "3" should read --2--.

Signed and Sealed this

Twenty-ninth Day of May, 2001

Attest:

NICHOLAS P. GODICI

Attesting Officer      Acting Director of the United States Patent and Trademark Office